US010323344B2

(12) United States Patent
Hartmann et al.

(10) Patent No.: US 10,323,344 B2
(45) Date of Patent: Jun. 18, 2019

(54) METHOD FOR MANUFACTURING A KNITTED FABRIC COMPRISING A VERTICAL YARN FILAMENT

(71) Applicant: H. STOLL AG & CO. KG, Reutlingen (DE)

(72) Inventors: Joerg Hartmann, Leonberg (DE); Francesco Collura, Kornwestheim (DE); Thomas Nonnenmacher, Pliezhausen (DE); Achim Ulmer, Reutlingen (DE)

(73) Assignee: H. Stoll AG & Co. KG, Reutlingen (DE)

( * ) Notice: Subject to any disclaimer, the term of this patent is extended or adjusted under 35 U.S.C. 154(b) by 179 days.

(21) Appl. No.: 15/643,620

(22) Filed: Jul. 7, 2017

(65) Prior Publication Data

US 2018/0010269 A1 Jan. 11, 2018

(30) Foreign Application Priority Data

Jul. 8, 2016 (DE) .......................... 10 2016 112 585

(51) Int. Cl.
*D04B 7/04* (2006.01)
*D04B 7/28* (2006.01)
(Continued)

(52) U.S. Cl.
CPC .............. *D04B 7/28* (2013.01); *A61B 5/6804* (2013.01); *D04B 7/04* (2013.01); *D04B 15/10* (2013.01);
(Continued)

(58) Field of Classification Search
CPC . D04B 1/10; D04B 1/12; D04B 1/123; D04B 7/04; D04B 7/14; D04B 7/28; D04B 15/48; D04B 15/56
See application file for complete search history.

(56) References Cited

U.S. PATENT DOCUMENTS 3,806,959 A * 4/1974 Gross ..................... D04B 21/16
66/192
3,986,530 A * 10/1976 Maekawa .......... A41D 31/0066
139/425 R (Continued)

FOREIGN PATENT DOCUMENTS

CN 203475074 U 3/2014
CN 203619561 U 6/2014

(Continued)

OTHER PUBLICATIONS

Chinese Office Action dated Nov. 13, 2018 in Chinese Application No. 201710551901.3 with English translation of the relevant parts.

*Primary Examiner* — Danny Worrell
(74) *Attorney, Agent, or Firm* — Collard & Roe, P.C.

(57) ABSTRACT

A method for manufacturing a knitted fabric embodying a basic knit, into which at least one functional yarn filament, such as an electrically conductive yarn filament, is incorporated as a vertical yarn filament (F3). The basic knit is formed from a first and a second yarn (F1, F2) using a plaiting technique. The vertical yarn filament (F3) is incorporated by a third yarn carrier (FF3) positioned, on a third yarn carrier rail located between respective yarn carrier rails for the first and the second yarn carriers (FF1, FF2), at a location at which the vertical yarn filament (F3) is to be incorporated. During formation of a sequence of stitch rows (MR1-MR7) using the first and second yarns (F1, F2), the first yarn (F1) is guided over the vertical yarn filament (F3) on a front side of the knitted fabric and the second yarn (F2) is guided over the vertical yarn filament (F3) on a back side of the knitted fabric.

10 Claims, 3 Drawing Sheets

(51) Int. Cl.
*A61B 5/00* (2006.01)
*D04B 15/10* (2006.01)
*D04B 15/48* (2006.01)
*D04B 15/56* (2006.01)
*A61B 5/01* (2006.01)
*A61B 5/024* (2006.01)

(52) U.S. Cl.
CPC ............ *D04B 15/48* (2013.01); *D04B 15/56* (2013.01); *A61B 5/01* (2013.01); *A61B 5/02438* (2013.01)

(56) References Cited

U.S. PATENT DOCUMENTS

| | | | | |
|---|---|---|---|---|
| 4,672,825 | A * | 6/1987 | Yasukawa | D04B 1/04 66/194 |
| 4,921,751 | A * | 5/1990 | Wakahara | B32B 27/12 139/420 A |
| 5,147,714 | A * | 9/1992 | Ellison | D03D 15/0005 66/195 |
| 5,428,969 | A * | 7/1995 | Day | D04B 1/12 66/202 |
| 5,615,562 | A * | 4/1997 | Roell | D04B 1/123 66/126 R |
| 6,151,922 | A * | 11/2000 | Shimasaki | D04B 1/02 66/190 |
| 6,854,296 | B1 * | 2/2005 | Miller, III | D04B 1/123 66/190 |
| 7,043,329 | B2 * | 5/2006 | Dias | D04B 7/32 66/55 |
| 8,476,172 | B2 * | 7/2013 | Christof | D04B 1/16 66/169 R |
| 2004/0014387 | A1 | 1/2004 | Sinykin | |
| 2006/0281382 | A1 * | 12/2006 | Karayianni | D03D 1/0088 442/181 |

FOREIGN PATENT DOCUMENTS

| | | |
|---|---|---|
| DE | 696 25 606 | 11/2003 |
| EP | 0 532 468 | 3/1993 |
| EP | 2 843 095 | 3/2015 |
| JP | 2000073202 A | 3/2000 |
| WO | WO 94/12711 | 6/1994 |

\* cited by examiner

METHOD FOR MANUFACTURING A KNITTED FABRIC COMPRISING A VERTICAL YARN FILAMENT

CROSS-REFERENCE TO A RELATED APPLICATION

The invention described and claimed hereinbelow is also described in German Patent Application DE 10 2016 112 585.7, filed on Jul. 8, 2016. The German Patent Application, the subject matter of which is incorporated herein by reference, provides the basis for a claim of priority of invention under 35 U.S.C. 119(a)-(d).

The invention relates to a method for manufacturing a knitted fabric comprising a basic knit, into which at least one functional yarn filament, such as an electrically conductive yarn filament, is incorporated as a vertical yarn filament, using a flat knitting machine comprising at least two needle beds.

For different areas of application, textiles must be equipped with additional functional elements such as sensors, data interfaces, heating elements, and/or LEDs, which require an electrical supply. These textiles, having an additional functionality, are referred to as so-called smart textiles. With the aid of integrated sensors, it is possible to detect, for example, temperature or pressure, the pulse or other bodily functions and movements of the wearer of the textile. The sensor data can be queried and further processed via data interfaces.

The power supply of the individual electrical components takes place via electrical conductive yarn filaments which are incorporated into the textiles. In the case of knitted fabrics, electrically conductive weft yarns, and/or vertical yarn filaments, can be incorporated via knitting and connected to form circuits. By use of the plaiting technique, weft yarns can be covered toward the outside, and so they do not adversely affect the appearance of the knitted fabric. Vertical yarn filaments, which extend in the vertical direction across the knitted fabric, cannot be woven along their entire length in such a way as to be non-visible from the outside, however, since they must be fastened on the knitted fabric at regular intervals by knitting stitches or tuck loops. If the vertical yarn filaments are to be completely covered toward the outside and are to be non-visible, a second layer must be knitted to cover them, which, however, increases the weight of the knitted fabric and therefore reduces the wearing comfort.

SUMMARY OF THE INVENTION

The present invention overcomes the shortcomings of known arts, such as those mentioned above.

The invention provides for incorporating vertical yarn filaments into knitted fabrics in such a way as to be non-visible from the outside, without the need to provide a further layer for this purpose.

In an embodiment, the invention provides a method for manufacturing a knitted fabric comprising a basic knit, into which at least one functional yarn filament, such as electrically conductive yarn filament, is incorporated as a vertical yarn, through use of a flat knitting machine comprising at least two needle beds. In the inventive method, the basic knit is formed with the aid of a first and a second yarn carrier, which are disposed on different yarn carrier rails in such a way as to be displaceable along the needle beds and in such a way as to simultaneously feed a first and a second yarn to the needles of the front and/or rear needle bed (plaiting technique), and in that the vertical yarn filament is incorporated by a third yarn carrier that is positioned, on a third yarn carrier rail located between the yarn carrier rails for the first and the second yarn carriers, at the desired position at which the vertical yarn filament is to be incorporated. During the formation of stitch rows using the first and second yarns, the first yarn is guided over the vertical yarn filament on the front side of the knitted fabric, and the second yarn is guided over the vertical yarn filament on the back side of the knitted fabric. As such, the first and second yarns cover the vertical yarn filament on the front side and the back side of the knitted fabric.

The vertical yarn filament is incorporated on the front side and the back side of the knitted fabric by the first and second yarns and is thereby securely fixed in the knitted fabric. As a result, it is not necessary to fasten the vertical yarn filament on the knitted fabric by knitting stitches or tuck loops. The basic knit can be knitted using any type of weave in this case.

Preferably, the first yarn is made visible on the front side of the knitted fabric and the second yarn is made visible on the back side of the knitted fabric. First and second yarns produced from the same material or from different materials can be utilized in this case. It is therefore possible to manufacture knitted fabrics having identical or different surface structures, colors or both on the front side and the back side.

It also is possible to incorporate a vertical yarn filament at multiple points on the knitted fabric, provided, for example, a mechanical reinforcement or reduction of the longitudinal elasticity of the knitted fabric is desired or if it should be necessary to incorporate multiple conductive vertical yarn filaments.

If the vertical yarn filament is not to be guided vertically, but rather diagonally or in a stepped pattern through the knitted fabric, the position of the third yarn carrier can be changed between the knitting of two stitch rows using the first and second yarns.

The desired angle at which the vertical yarn filament is to extend through the knitted fabric can be adjusted via the size of the offset of the third yarn carrier between adjacent stitch rows. A zigzag course or a course in a stepped pattern of the vertical yarn filament can be implemented as a result.

In the case of electrically conductive vertical yarn filaments, the vertical yarn filament cannot be covered by the first or the second yarn in one or multiple stitch rows, so that the vertical yarn filament can be contacted by an electrical consumer, for example an LED or the like. It should be noted, however, that making the vertical yarn filament visible, in such a way, at individual points also can be carried out for purely appearance-related reasons.

If the vertical yarn filament is to extend through the knitted fabric even from the beginning, the third yarn carrier can be brought into the desired position even before the formation of the first stitch row for the knitted fabric using the first and second yarns. The vertical yarn filament also can be first incorporated in a middle area of the knitted fabric by displacing the third yarn carrier into the desired position, i.e., after the formation of a few stitch rows for the basic knit solely by the first and second yarns.

All the yarn carriers, for example, the third yarn carrier, can be standard yarn carriers, plaiting yarn carriers, or intarsia yarn carriers, and can either be moved by the carriage of the knitting machine or can be autonomously driven.

For knitted fabrics comprising integrated electrical components, closed electrical circuits can be manufactured in the knitted fabric with the aid of conductive vertical yarn filaments and weft yarns. Electrical consumers such as sensors or LEDs can therefore be supplied with current. In addition to electrical consumers and switches, the circuit also can be connected to a battery that is integrated in the knitted fabric and can be accommodated, for example, in a knitted pocket of the knitted fabric.

It also is possible, of course, to connect the circuit or circuits to external current sources.

BRIEF DESCRIPTION OF THE DRAWINGS

Further features and advantages of the invention will become apparent from the description of embodiments that follows, with reference to the attached figures, wherein.

DETAILED DESCRIPTION OF THE PREFERRED EMBODIMENTS

The following is a detailed description of example embodiments of the invention depicted in the accompanying drawings. The example embodiments are presented in such detail as to clearly communicate the invention and are designed to make such embodiments obvious to a person of ordinary skill in the art. However, the amount of detail offered is not intended to limit the anticipated variations of embodiments; on the contrary, the intention is to cover all modifications, equivalents, and alternatives falling within the spirit and scope of the present invention, as defined by the appended claims.

Figure 1:
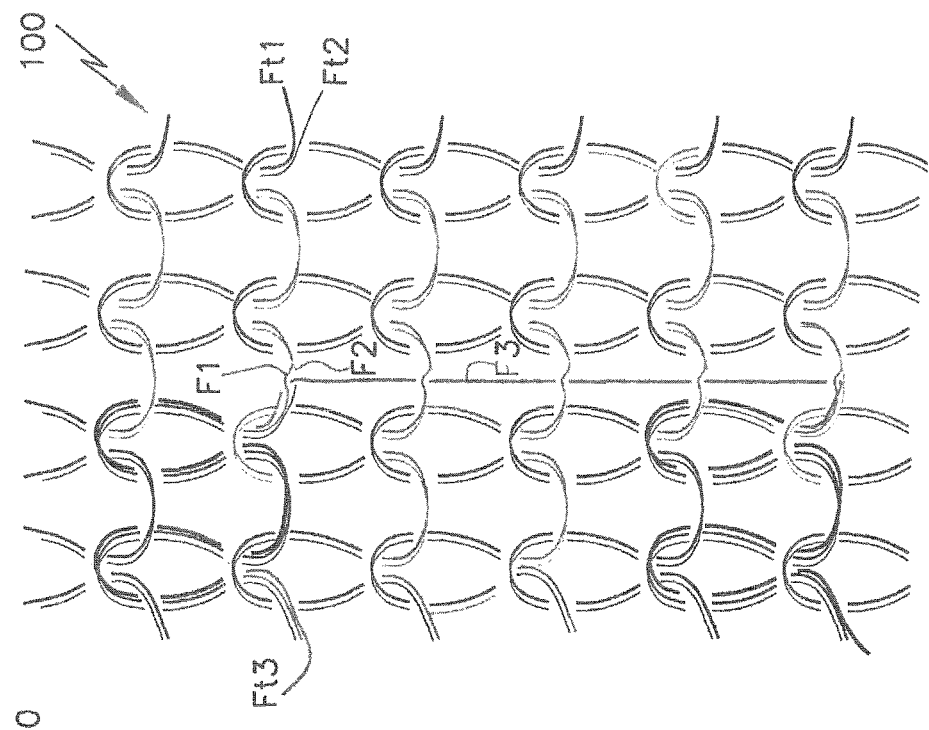
FIG. 1 depicts a section of the right side of a knitted fabric, including a vertical yarn filament, in a representation of the knitting stitches.

FIG. 1 shows a section of the right side of a knitted fabric 100, which, in the example shown, is a basic knit comprising seven knitted rows MR1 through MR7, each of which includes four knitting stitches a-d. The knitting stitches of the stockinette-stitched basic knit are formed from two yarns F1 and F2. Two separate yarn carriers FF1 and FF2 (not shown), which are guided on different rails and one after the other, are utilized for this purpose. The yarns F1 and F2 can be identical or different. An offset of the yarn carriers FF1 and FF2 can be utilized to determine which yarn F1, F2 is visible on the right side of the fabric and which yarn F1, F2 is visible on the left side of the fabric (plaiting technique). A third yarn F3 is introduced into the basic knit in the stitch row MR2 by a third yarn carrier (not shown) via intermeshing (plaiting) in the knitting direction from left to right. The yarn F3, together with the yarns F1 and F2, forms the knitting stitches a and b.

Figure 2:
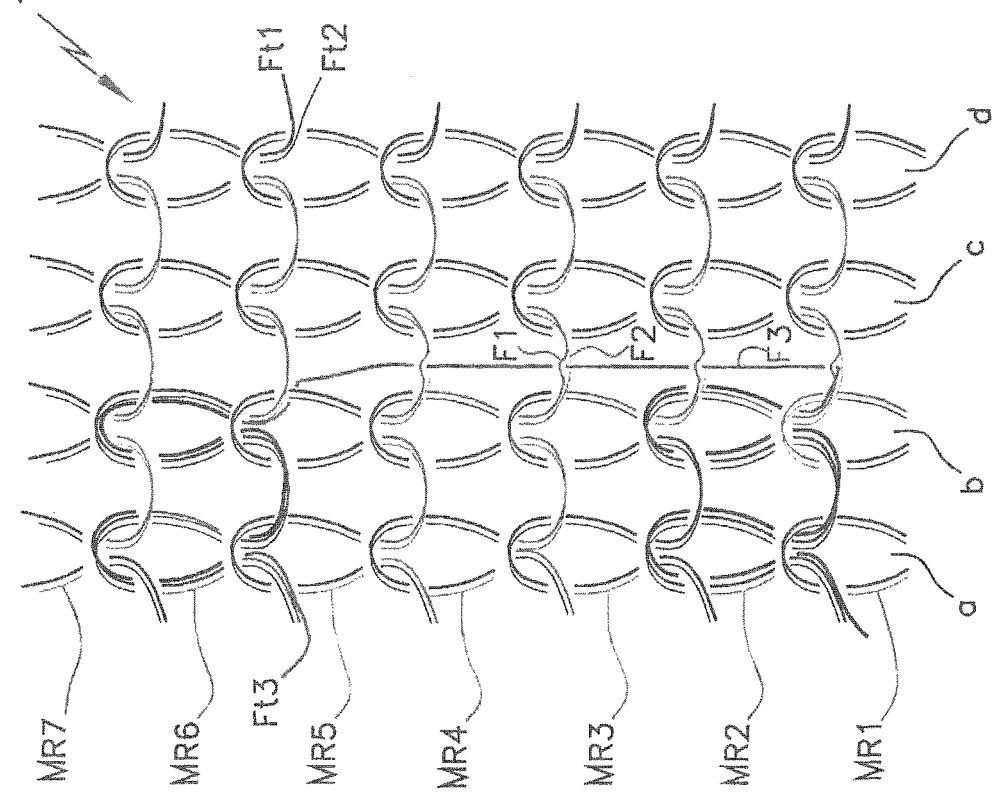
FIG. 2 presents a view of the left side of the knitted fabric from FIG. 1, in a representation of the knitting stitches.

Subsequent thereto, the yarn carrier FF3 is stopped between knitting stitches b and c. The yarn carrier FF3 (not shown) is located on a separate yarn carrier rail, which is disposed between the yarn carrier rails of the yarn carriers FF1 and FF2. The yarn F3 also can be incorporated into the basic knit using other known knitting methods, for example, an intarsia knitting method. As shown in FIG. 1, the yarn F3 is enclosed by the yarns F1 and F2 in the knitting rows MR2 to MR5, i.e., the yarn F1 is guided over the yarn F3 on the right side of the knitted fabric 100, and the yarn F2 is guided over the yarn F3 on the left side of the fabric, as is also illustrated in FIG. 2. Since the yarns F1 and F2 are wrapped around the yarn F3, the yarn F3 is securely fixed in the knitted fabric 100.

In the stitch row MR6, the yarn carrier FF3 is displaced from right to left and, together with the yarn F3 and the yarns F1 and F2, forms knitting stitches b and a and, as a result, the yarn F3 is guided out of the basic knit again. Between the stitch rows MR2 and MR6, the yarn F3 extends vertically, as a vertical yarn filament, through the knitted fabric 100.

Figure 3:
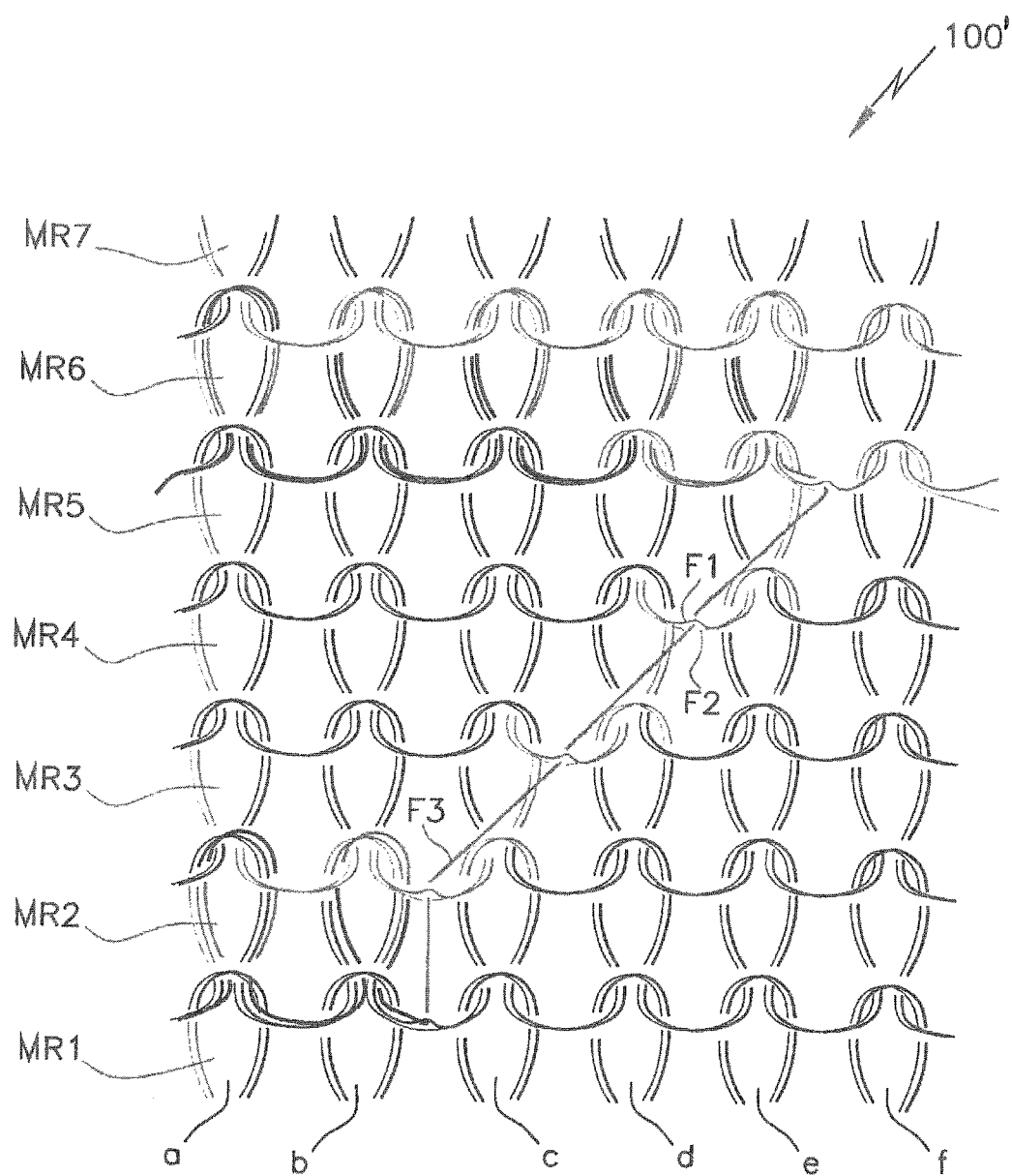
FIG. 3 presents a section of the left side of a knitted fabric including a diagonally extending vertical yarn filament.

FIG. 3 shows a section of a knitted fabric 100' from the left side of the fabric. In this example, the knitted fabric 100' comprises a basic knit including seven stitch rows MR1 through MR7, each including six knitting stitches a-f, which are formed by yarns F1 and F2 in this case as well, using the plaiting technique. A vertical yarn filament F3 is introduced into the basic knit again, which extends from the stitch row M2 diagonally through the knitted fabric 100' in this case, however. This is achieved by offsetting the yarn carrier FF3 for the vertical yarn filament F3 toward the right by one needle after each stitch row MR2 through MR4. Flatter angles for the course of the yarn F3 can also be achieved by means of a greater offset of the yarn carrier FF3 between the individual stitch rows.

In the example shown, the yarns F1 and F2 wrap around the yarn F3 between the knitting stitches b and c in stitch row MR2, the yarns F1 and F2 wrap around the yarn F3 between the knitting stitches c and d in stitch row MR3, the yarns F1 and F2 wrap around the yarn F3 between the knitting stitches d and e in stitch row MR4, and the yarns F1 and F2 wrap around the yarn F3 between the knitting stitches e and f in stitch row MR5. The vertical yarn filament F3 can be inserted and removed in the same way as for the knitted fabric 100 from FIGS. 1 and 2.

Figure 4:
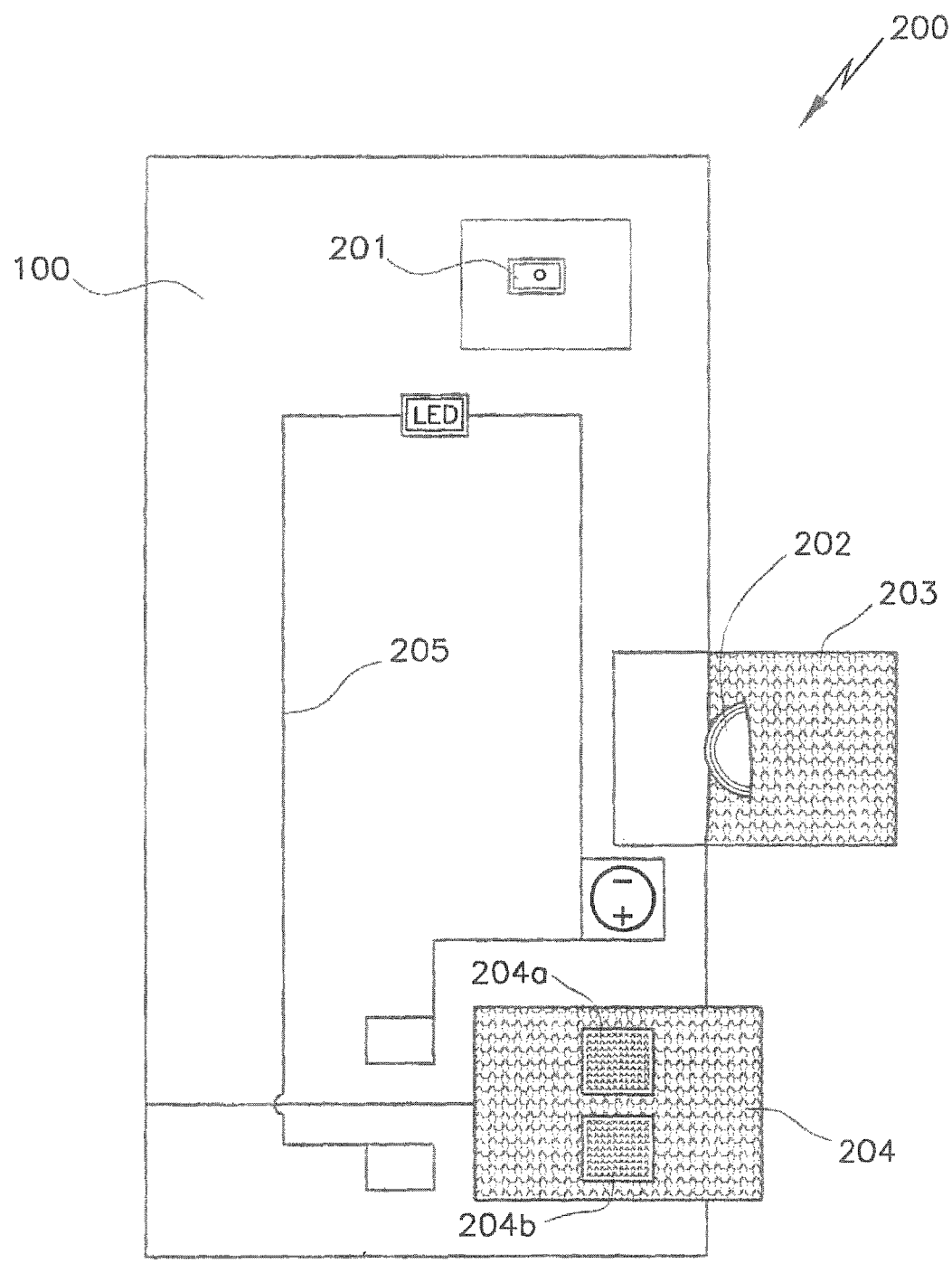
FIG. 4 is a schematic representation of an electrical circuit integrated into a knitted fabric.

FIG. 4 shows a schematic representation of a circuit 200, which can be introduced, for example, into the knitted fabric 100 (FIGS. 1 and 2), or fabric 100' (FIG. 3) using a method according to the invention. The circuit comprises an LED 201, which has been introduced into the basic knit and which is supplied with current by a battery in the form of a button cell 202. The button cell 202 is accommodated in a pocket 203 integrated into the knitted fabric 100, 100'.

To interrupt the electrical circuit, a switch 204 is disposed in the basic knit, which has been knitted from a conductive yarn material. The areas 204a, 204b, which were formed from the conductive yarn material, can be placed one on top of the other or can be separated from each other to close or interrupt the electrical circuit.

The individual components 201, 202 and 204 are connected to each other via electrically conductive vertical yarn filaments F3 and electrically conductive weft yarns (not shown).

As will be evident to persons skilled in the art, the foregoing detailed description and figures are presented as examples of the invention, and that variations are contemplated that do not depart from the fair scope of the teachings and descriptions set forth in this disclosure. The foregoing is not intended to limit what has been invented, except to the extent that the following claims so limit that.

What is claimed is:

1. A method for manufacturing a knitted fabric comprising a basic knit, into which at least one electrically conductive yarn filament is incorporated as a vertical yarn filament (F3), using a flat knitting machine having at least two needle beds and in reliance upon a first and a second yarn carrier (FF1, FF2), which are arranged on different yarn carrier rails to be displaceable along the at least two needle beds, the method comprising the steps of:

using the first and the second yarn carrier (FF1, FF2) to simultaneously feed a first and a second yarn (F1, F2) to needles of a front needle bed, a rear needle bed or both, of the at least two needle beds;

incorporating the electrically conductive vertical yarn filament, using a third yarn carrier (FF3) positioned on a third yarn carrier rail located between the yarn carrier rails for the first and the second yarn carriers (FF1, FF2), at the desired position at which the vertical yarn filament (F3) is to be incorporated; and forming a sequence of stitch rows (MR1-MR7) using the first and second yarns (F1 F2), by guiding the first yarn (F1) over the electrically conductive vertical yarn filament (F3) on a front side of the knitted fabric, and guiding the second yarn over the electrically conductive vertical yarn filament (F3) on a back side of the knitted fabric, such that the first and second yarns (F1, F2) cover the electrically conductive vertical yarn filament (F3) on the front side and the back side of the knitted fabric.

2. The method according to claim 1, wherein in the step of forming, making the first yarn (F1) visible on the front side of the knitted fabric and making the second yarn (F2) visible on the back side of the knitted fabric.

3. The method according to claim 1, wherein the first and second yarns (F1, F2) are produced from the same material or from different materials.

4. The method according to claim 1, wherein the electrically conductive vertical yarn filament (F3) is incorporated at multiple points of the knitted fabric.

5. The method according to claim 1, wherein the step of forming includes that changing a position of the third yarn carrier (FF3) between the knitting of two stitch rows of the sequence of stitch rows (MR1-MR7), using the first and second yarns (F1, F2).

6. The method according to claim 1, wherein the step of forming includes that the electrically conductive vertical yarn filament (F3) is not covered by the first or the second yarn (F1, F2) in one or multiple stitch rows of the sequence of stitch rows (MR1-MR7).

7. The method according to claim 1, wherein the step of forming includes that the third yarn carrier (FF3) is brought into the desired position prior to formation of the first stitch row (MR1) for the knitted fabric, by use of the first and second yarns (F1, F2).

8. The method according to claim 1, wherein a standard yarn carrier or a plaiting yarn carrier is utilized as the third yarn carrier (FF3), and wherein the third yarn carrier (FF3) is moved by the carriage of the knitting machine or driven autonomously.

9. The method according to claim 1, further comprising a step of producing a closed electrical circuit in the knitted fabric in reliance upon one or more of the electrically conductive vertical yarn filament and weft yarns.

10. The method according to claim 9, further comprising a step of electrically connecting batteries, switches, and consumers such as LEDs to the closed electrical circuit produced in the knitted fabric.

* * * * *